United States Patent [19]

Briend et al.

[11] Patent Number: 5,651,358
[45] Date of Patent: Jul. 29, 1997

[54] NITRIC OXIDE VENTILATION ARRANGEMENT AND METHOD

[75] Inventors: Robert Briend, Les Clayes-Sous-Bois; Marie-Hélène Renaudin, Paris, both of France

[73] Assignee: L'Air Liquide, Societe Anonyme Pour L'Etude et L'Exploitation des Procedes Georges Claude, Paris Cedex, France

[21] Appl. No.: 439,442

[22] Filed: May 11, 1995

Related U.S. Application Data

[63] Continuation of Ser. No. 119,674, Sep. 13, 1993, abandoned.

[30] Foreign Application Priority Data

Sep. 24, 1992 [FR] France .................... 92 11370

[51] Int. Cl.⁶ .............. A61M 15/00; A61M 16/10; F16K 11/00; A62B 7/00
[52] U.S. Cl. ............... 128/203.12; 128/204.18; 128/203.25; 128/204.22
[58] Field of Search ............ 128/200.16, 200.24, 128/203.12, 203.14, 204.18, 204.22, 204.26, 204.25, 203.25, 205.24

[56] References Cited

U.S. PATENT DOCUMENTS

| | | | |
|---|---|---|---|
| 4,148,312 | 4/1979 | Bird | 128/204.25 |
| 4,150,670 | 4/1979 | Jewett et al. | 128/204.22 |
| 4,442,856 | 4/1984 | Betz | 137/98 |
| 4,576,159 | 3/1986 | Hahn | 128/203.14 |
| 4,702,240 | 10/1987 | Chaoui | 128/204.18 |
| 4,903,693 | 2/1990 | Yasue | 128/203.12 |
| 4,905,683 | 3/1990 | Olsson et al. | 128/203.12 |
| 4,932,401 | 6/1990 | Perkins | 128/203.12 |
| 5,237,990 | 8/1993 | Psaros et al. | 128/204.21 |
| 5,239,994 | 8/1993 | Atkins | 128/204.18 |
| 5,396,882 | 3/1995 | Zapol | 128/202.25 |
| 5,485,827 | 1/1996 | Zapol et al. | 128/200.23 |
| 5,522,381 | 6/1996 | Olsson et al. | 128/203.25 |
| 5,531,218 | 7/1996 | Krebs | 128/203.25 |

FOREIGN PATENT DOCUMENTS 0183593  6/1986  European Pat. Off. .
1912572  1/1973  Germany .

*Primary Examiner*—Kimberly L. Asher
*Attorney, Agent, or Firm*—Young & Thompson

[57] ABSTRACT

The mouthpiece (2) of a respirator (1) is connected to a bottle (8) of a gaseous mixture containing nitric oxide by a line (10) comprising an electrovalve (18) controlled (17) by a signal representing a supply (7, 15, 12) of a flow of respiratory mixture by the respirator (1). The installation is controlled so as to supply, upon inhalation, a gaseous mixture comprising between 21 and 100% of oxygen and between 10 and 50 ppm of nitric oxide.

13 Claims, 1 Drawing Sheet

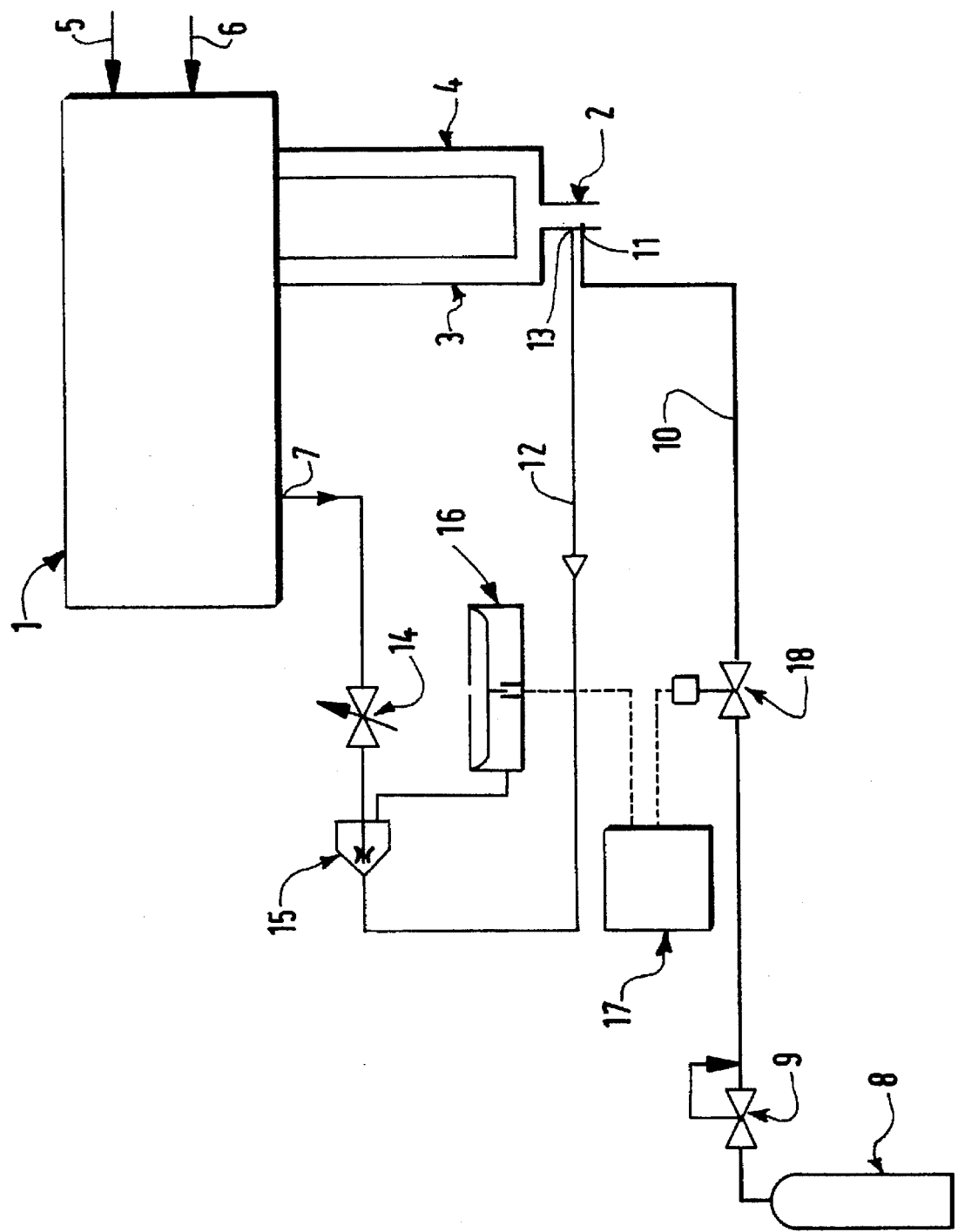

NITRIC OXIDE VENTILATION ARRANGEMENT AND METHOD

This application is a continuation of application Ser. No. 08/119,674, filed Sep. 13, 1993, now abandoned.

FIELD OF THE INVENTION

The present invention relates to an installation for providing a gaseous mixture to the respiratory passages of a user, comprising a device, or respirator, for providing sequentially a respiratory mixture in a utilization conduit, the device comprising detection means for the inhalation phases of the user.

BACKGROUND OF THE INVENTION

An installation of this type, to supply under controlled pressure oxygen or air enriched in oxygen to the respiratory passages of a user is described in the document EP-A-347.282. Existing installations of this type are preferably complemented by an auxiliary outlet for a respiratory mixture under pressure to connect to a nebulization circuit introducing droplets of active product into the respiratory mixture during the inhalation phases:

It has been recently noted that nitric oxide, administered by inhalation, has pulmonary vaso-dilatory properties which can be quite useful for controlling symptoms of respiratory distress in adults and newborn or for maintaining the vital functions during surgical interventions in the heart-lung area. However, in the presence of oxygen, nitric oxide oxidizes rapidly to form nitrogen dioxide, which can lead to the formation of toxic metabolites.

SUMMARY OF THE INVENTION

The present invention has for its object to provide an improved installation of the above type permitting supplying, in a simple and reliable manner and with total safety, controlled quantities of nitric oxide substantially directly into the respiratory passages of the patient, without preliminary and significant premixing with the oxygen of the usual respiratory mixture, and during only the inhalation phases.

To do this, according to one characteristic of the invention, the installation comprises means, acting in response to the control means of the respirator, to add quantities of nitric oxide to the respiratory mixture in the utilization conduit.

According to other characteristics of the invention:
the addition means for the nitric oxide comprise a distribution line between a source of nitric oxide and the utilization conduit, this line comprising a device for regulation sensitive to the delivery of a flow of respiratory mixture by the supply device for the respiratory mixture;
the device for regulating the supply of nitric oxide comprises means for the detection of the passage of a flow in a supplemental outlet line for respiratory mixture of the supply device.

The present invention has for another object a process for the supply of a gaseous mixture to the respiratory passages of a user, comprising the steps of supplying, in response to a detection, generated by the user or by the respirator, of a beginning of an inhalation phase, a gaseous mixture comprising at least 21%, typically between 50 and 100% of oxygen, and at most 50 ppm, typically between 10 and 50 ppm of nitric oxide, the balance being nitrogen.

BRIEF DESCRIPTION OF THE DRAWING

Other characteristics and advantages of the present invention will become apparent from the following description of an embodiment, given by way of illustration but in no way limiting, with respect to the accompanying drawing, in which:

The single FIGURE represents schematically an installation according to the invention.

DETAILED DESCRIPTION OF THE INVENTION

In the single FIGURE, there will be seen a device for supplying a respiratory mixture or respirator 1, such as described in the document EP-A-347.282 above-mentioned, coupled to an intubation tube or a utilization mouthpiece 2 by an inhalation branch 3 and an exhalation branch 4 connected at the level of the mouthpiece 2. The respirator 1 comprises a device for detection of the beginning of the respiratory phase (not shown), an oxygen inlet 5, an air inlet 6 and an outlet 7 of an auxiliary flow of respiratory air/oxygen mixture.

According to the invention, the installation comprises a bottle 8 containing an inert gas, typically nitrogen, and a small quantity of nitric oxide, less than 250 ppm, typically about 225 ppm, provided with an expander 9, and connected, by a line 10, to a point 11 in the downstream portion of the mouthpiece or tube 2. The supplemental outlet of the respirator 1 is connected by a line 12 to the tube 2 at a point 13 upstream of the outlet 11 of the line 10. The line 12 comprises a control valve 14 and a Venturi expansion sensor 15 coupled to a pressure transducer 16 supplying a signal to an electronic regulation unit 17 controlling an electrovalve 18 interposed in the line 10, downstream of the expander 9.

During an inhalation phase of the patient, the respirator 1 supplies to the inhalation branch 3 and to the outlet 7 a respiratory mixture of air enriched in oxygen. The flow of this respiratory mixture in the line 12 gives rise, in the sensor 15, to an underpressure which is detected by the transducer 16 and which controls the opening of the electrovalve 18 to add, to the flow of respiratory mixture supplied by the respirator 1 to the tube 2, a controlled quantity of nitric oxide. The electrovalve 18, of the normally closed type, is opened by the control unit 17, at the beginning of the inhalation phase, for a period which can be varied for example between 0.1 and 1 second, the duration of opening and the pressure, fixed by the expander 9, being determined so as to obtain the desired concentration of nitric oxide as a function of the current inhalation volume of the user, typically between 10 and 40 ppm. The pressure transducer 16 is preferably of the differential membrane type, as described in the document EP-A-183,593, in the name of the assignee.

In the preceding description, it will be understood that the circuit for the injection of nitric oxide, which can be used with any type of pre-existing respirator, is totally independent of the respiratory gas circuits of the respirator 1, which avoids any risk of the introduction of nitric oxide into this latter, and that its injection is effected as far downstream as possible in the inhalation circuit of the patient, thereby to minimize the risks of oxidation of nitric oxide by the oxygen present as the majority of the respiratory mixture supplied to the patient, by the respirator 1.

Although the present invention has been described with respect to one particular embodiment, it is not thereby limited but is on the contrary susceptible of modifications and variations which will be apparent to one skilled in the art.

What is claimed is:

1. A system for supplying gas to the respiratory ways of a patient, comprising:
   at least one source of a breathable oxygenated gas mixture under pressure;
   a source of nitric oxide under pressure;
   a gas conduit having an upstream portion connected to a respiratory device and a downstream portion adapted to be connected to the respiratory ways;
   a respiratory device connected to the sources of oxygenated gas mixture and of nitric oxide and including detection means for detecting inhalation phases of the patient and means for sequentially supplying to the gas conduit doses of said oxygenated gas mixture at a first point located upstream of the gas conduit and a controlled amount of nitric oxide at a second point located in the downstream portion of the conduit, upstream of the respiratory ways, and downstream of said first point, whereby premixing and oxidation of the nitric oxide with the oxygenated gas mixture is minimized before inhalation of the gas by the patient.

2. The system of claim 1, comprising a delivery line extending from the source of nitric oxide and opening into the gas conduit.

3. The system of claim 2, wherein the delivery line includes a delivery device coupled to a control device responsive to the delivery of a flow of said oxygenated gas mixture to the gas conduit.

4. A method of supplying gases to the respiratory ways of a patient, comprising:
   providing a breathable oxygenated gas mixture;
   providing an active gas mixture containing nitric oxide;
   providing a gas conduit having an upstream portion connected to a respiratory device and a downstream portion adapted to be connected to the respiratory ways;
   providing a respiratory device connected to the sources of oxygenated gas mixture and of nitric oxide;
   sequentially supplying a flow of said oxygenated gas mixture to the respiratory ways at a first point located upstream of the gas conduit; and
   introducing a controlled amount of said active gas mixture into said flow of oxygenated gas mixture, said controlled amount of nitric oxide being introduced at a second point located in the downstream portion of the conduit upstream of the respiratory ways but downstream of the first point, whereby premixing and oxidation of the nitric oxide with the oxygenated gas mixture is minimized before inhalation of the gases by the patient.

5. The method of claim 4, wherein the active gas mixture contains less than 250 ppm of nitric oxide.

6. The method of claim 5, wherein the amount of nitric oxide introduced in the flow of oxygenated gas mixture is between 10 and 50 ppm.

7. The method of claim 6, wherein the oxygenated gas mixture contains not less than 50% of oxygen.

8. An installation for supplying a gaseous mixture to the respiratory passages of a user, comprising a respiratory mixture delivery conduit having an upstream portion and a downstream portion, a supply device including means for sequentially supplying a respiratory mixture at a first point upstream of the respiratory mixture delivery conduit and detection means for the inhalation phases of the user, addition means including a source of nitric oxide for adding controlled quantities of nitric oxide at a second point in the downstream portion of the respiratory mixture delivery conduit, said second point being located upstream of the respiratory passages but downstream of said first point whereby premixing and oxidation of the nitric oxide with the respiratory mixture is minimized before inhalation of the gaseous mixture by the user, said addition means acting in response to the detection means and comprising a line between the respiratory mixture delivery conduit and the source of nitric oxide, said line including a control device sensitive to the flow of respiratory mixture delivered by the supply device, said supply device including a supplemental outlet for respiratory mixture, and said control device including means for sensing flow of respiratory mixture through the supplemental outlet.

9. An installation according to claim 8, wherein the sensing means comprise a pressure reduction device connected to the supplemental outlet and coupled to a pressure sensor.

10. An installation according to claim 9, wherein the pressure sensor is of the differential membrane type.

11. An installation according to claim 8, wherein the source of nitric oxide comprises a reservoir provided with an expander.

12. An installation according to claim 11, wherein the reservoir contains a mixture of nitrogen and nitric oxide, said nitrogen oxide being present in the mixture in an amount not exceeding 250 ppm.

13. An installation according to claim 8, wherein the supply device for respiratory gas is fluidly connected to a source of oxygen.

* * * * *